US007244558B1

(12) United States Patent
Samal et al.

(10) Patent No.: US 7,244,558 B1
(45) Date of Patent: Jul. 17, 2007

(54) PRODUCTION OF NOVEL NEWCASTLE DISEASE VIRUS STRAINS FROM CDNAS AND IMPROVED LIVE ATTENUATED NEWCASTLE DISEASE VACCINES

(75) Inventors: Siba K. Samal, College Park, MD (US); Peter L. Collins, Kensington, MD (US)

(73) Assignees: University of Maryland, College Park, MD (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 09/926,431

(22) PCT Filed: May 5, 2000

(86) PCT No.: PCT/US00/06700

§ 371 (c)(1),
(2), (4) Date: Mar. 6, 2002

(87) PCT Pub. No.: WO00/67786

PCT Pub. Date: Nov. 16, 2000

Related U.S. Application Data

(60) Provisional application No. 60/171,072, filed on Dec. 16, 1999, provisional application No. 60/132,597, filed on May 5, 1999.

(51) Int. Cl.
| | |
|---|---|
| *C12Q 1/70* | (2006.01) |
| *C12Q 1/68* | (2006.01) |
| *C12N 7/04* | (2006.01) |
| *C12N 7/02* | (2006.01) |

(52) U.S. Cl. .............................. 435/5; 435/6; 435/236; 435/239
(58) Field of Classification Search ............. 424/214.1, 424/186.1, 199.1, 202.1, 204.1, 93.2, 23.1, 424/23.72; 536/23.1, 23.72
See application file for complete search history.

(56) References Cited

U.S. PATENT DOCUMENTS 6,146,642 A    11/2000    Garcia-Sastre et al.

6,451,323 B1    9/2002    Garcia-Sastre et al.

FOREIGN PATENT DOCUMENTS

WO    PCT/NL99/00377    *    6/1999

OTHER PUBLICATIONS

Millar et al., (Journal of General Virology 1988, 69, 613-620).*
Stone, H. D., Avian Diseases vol. 33, pp. 157-162, 1989.*
Schijns et al., (Vaccine, vol. 18, pp. 2147-2154, 2000).*
Biotech Dictionary: attenuated.*
Yusoff, K. et al., "Location of Neutralizing Epitopes on the Fusion Protein of Newcastle Disease Virus Strain Beaudette C", J. Gen. Virol. 1989, vol. 70, pp. 3105-3109.
Krishnamurthy, S. et al., "Nucleotide Sequences of the Trailer, Nucleocapsid Protein gene and Intergenic regions of Newcastle Disease Virus Strain Beaudette C and Completion of the Entire Genome Sequence", Journal of General Virology, 1998, vol. 79, pp. 2419-2424.
Schaper, U.M. et al., "Nucleotide Sequence of the Envelope Protein genes of a Highly Virulent, Neurotropic strain of Newcastle Disease Virus", Virology, 1988, vol. 165, pp. 291-295.
Yusoff, K. et al., "Nucleotide Sequence Analysis of the L Gene of Newcastle Disease Virus: Homologies with Sendai and Vesicular Stomatitis Viruses", Nucleic Acids Research 1987, vol. 15, No. 10, pp. 3961-3976.
Daskalakis, S. et al., "Nucleotide Sequence of the Phosphoprotein (P) Gene of Newcastle Disease Virus (Strain Beaudette C)", Nucleic Acids Research, 1992, vol. 20, No. 3, p. 616.

* cited by examiner

*Primary Examiner*—Bruce R. Campell
*Assistant Examiner*—Sharon Hurt
(74) *Attorney, Agent, or Firm*—Arent Fox LLP

(57) ABSTRACT

The present invention concerns cDNAs for making attenuated, infectious Newcastle disease virus (NDV). Another aspect of the invention relates to methods of making the cDNAs. Another aspect of the invention is a vector containing the cDNA optionally linked to an operable promoter. Within the scope of the invention are vaccines comprising the attenuated, infectious NDV. Also disclosed are methods of making the vaccines and methods of using the vaccines to prevent or treat Newcastle disease in an avian host. The present invention also concerns the nucleotide sequences of the entire genome of NDV, the leading region, the trailing region, and the NP region, as well as proteins encoded by these nucleotide sequences.

10 Claims, 17 Drawing Sheets

```
                                                                              55
D26 Leader        3' UGGUUUGUCUCUUAGACAUUCAAUGCUAUUUUCCGCUUCCUCGUUAGCUUCAGCAUGCCCAUCUU
                     ................   .....  ..........................  ..... .
Beaudette C Leader 3' UGGUUUGUCUCUUAGGCAUUCAAUGCUAUUUUCCGCUUCCUCGUUAACUUCAACGUGCCCAUCUU
                     ..............................................................  ...
B1 Leader         3' UGGUUUGUCUCUUAGGCACUCAAUGCUAUUUUCCGCUUCCUCGUUAACUUCAGCGUGCCCAUCUU
                                                                              NP gene start
```

(b)

```
                                                                              58
Beaudette C Trailer 3' _AACUUGAGGCUGAGGAAUCUAGAGCUUAAGCUUGAGUUUAUUUACAGAAUUUUUUUC
                        ....  ...  ..........     ........................... .......
B1 Trailer          3'  CAACUCCAGACUGAGGAAUCCUGAGCUUGAGCUUGAGUUUAUUUACAGAAAUUUUUUC
                        59
Beaudette C Trailer     CAACGCGUGUUAAUAAGAACUCACAUCAGAACAAUAAGUGGUUUAGAAACAAACCA 5' 113
                        .............................. ..  ......................
B1 Trailer              CAACGCGUGUUAAUAAGAACUCACAUCAGAGCAGUAAGUGGUUUAGAAACAAACCA 5' 114
```

FIGURE 4

FIGURE 5
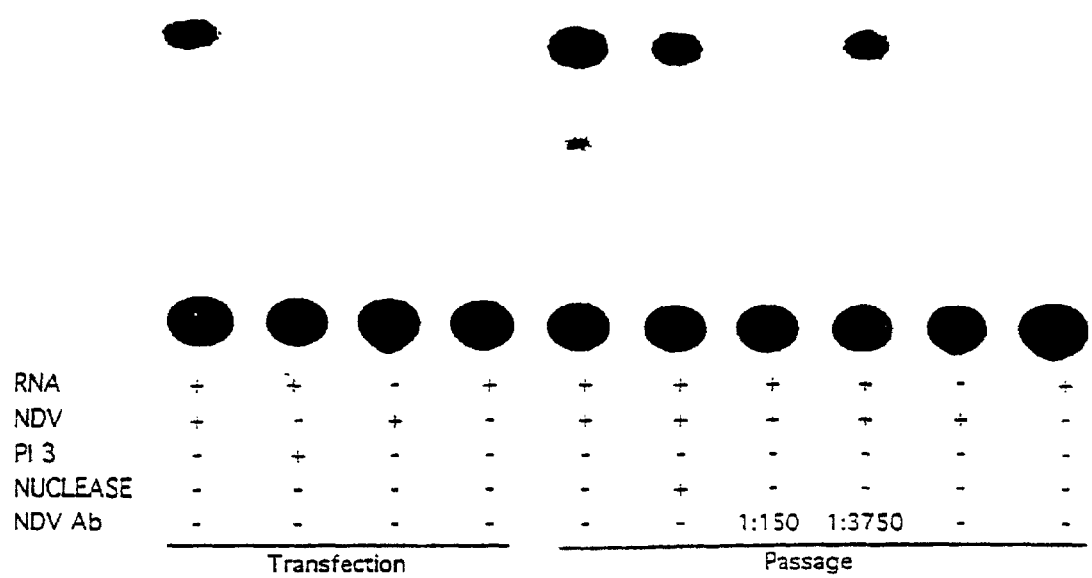
Fig. 5A  Demonstration of NDV minigenome transcription by CAT activity.
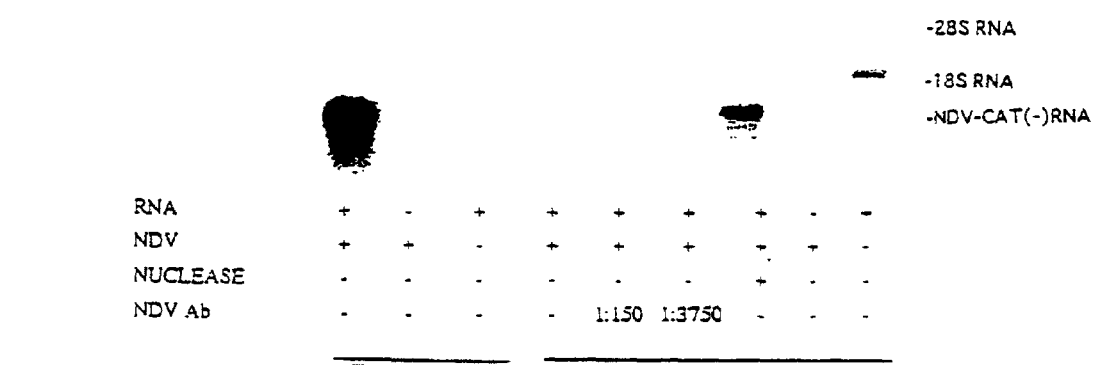
Fig. 5B  Demonstration of NDV minigenome replication by Northern hybridization.

FIGURE 7

| | | | | |
|---|---|---|---|---|
| NP | − | + | − | + |
| P | − | + | − | + |
| L | − | + | − | + |
| NDV-CAT(−) | − | − | + | + |
| VTF7-3 | + | + | + | + |

FIGURE 9 p+ NDV — Transfect

Vaccinia MVA/T7 — Infect

Support plasmids: NP, P, L — Transfect

HEp2 Cell 3 days

INFECTIOUS NDV

FIGURE 10
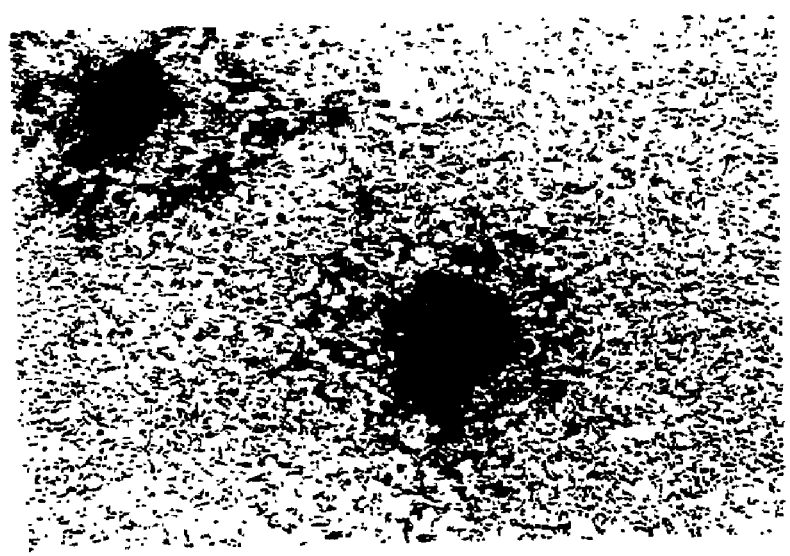
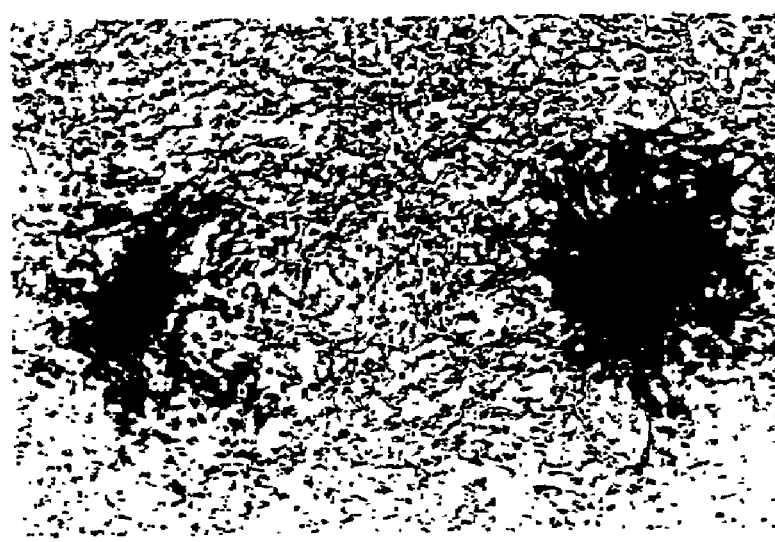

FIGURE 12

CLEAVAGE SITE

```
              110        116   117                                    142
Lentogenic    G G G R Q G R   L I G A I I G G V A L G V A T A A Q I T A A A A L I Beaudette C   G G R R Q K R   F I G A I I G G V A L G V A T A A Q I T A A A A L I ⎡ 1.       G   G     L
            │ 2.       G
  MUTANTS  ─┤ 3.           G
            │ 4.                 L
            │ 5.       G   G
            │ 6.       G         L
            ⎣ 7.           G     L
```

FIGURE 13

NDV(BC)CAT antigenomic RNA

PRODUCTION OF NOVEL NEWCASTLE DISEASE VIRUS STRAINS FROM CDNAS AND IMPROVED LIVE ATTENUATED NEWCASTLE DISEASE VACCINES

CROSS-REFERENCE TO RELATED APPLICATION

This application is a National Stage entry of International Application No. PCT/US00/06700, filed May 5, 2000, which claims priority from U.S. Provisional Application Ser. Nos. 60/132,597, filed May 5, 1999 and 60/171,072, filed Dec. 16, 1999, the entire specification claims and drawings of each are incorporated herewith by reference.

The present invention relates to Newcastle disease virus (NDV). In particular, the invention concerns the production of novel NDV strains from cDNAs and the production of improved Newcastle disease vaccines.

BACKGROUND OF THE INVENTION

Newcastle disease virus (NDV) causes a highly contagious and fatal disease affecting all species of birds. Newcastle disease can vary from mild to highly virulent depending upon the virus strain and the host species (1). The virus is a member of the family Paramyxoviridae (2) and contains a single-stranded negative-sense RNA genome.

The genome of NDV is a single strand negative-sense RNA, which has been founded to consist of 15,186 nucleotides (3). The genomic RNA contains six structural genes, which encode at least seven proteins (4,5). Three proteins constitute the nucleocapsid; specifically the nucleoprotein (NP), the phosphoprotein (P), and the large polymerase protein (L). Two proteins form the external envelope spikes, namely the F and HN proteins. The matrix protein (M) forms the inner layer of the virion. The genomic RNA is tightly bound by the NP protein and with the P and L proteins form the functional nucleocapsid within which resides the viral transcriptive and replicative activities. The HN glycoprotein is responsible for attachment of virus to host cell receptors and the F glycoprotein mediates fusion of the viral envelope with the host cell plasma membrane thereby enabling penetration of viral genome into cytoplasm (6). The HN and F proteins are the main targets for the immune response (7, 8). In common with several other Paramyxoviruses, NDV produces a seventh protein (V) of unknown function by editing of the P gene (5, 9).

NDV follows the general scheme of transcription and replication of other nonsegmented negative-strand RNA viruses. The polymerase enters the genome at a promoter in the 3' extragenic leader region and proceeds along the entire length by a sequential stop-start mechanism during which the polymerase remains template bound and is guided by short consensus gene-start (GS) and gene-end (GE) signals. This generates a free leader RNA and six nonoverlapping subgenomic mRNAs. The abundance of the various mRNAs decreases with increasing gene distance from the promoter. The genes are separated by short intergenic regions (1-47 nucleotides) which are not copied into the individual mRNAs. The 3' terminus (leader) and the 5' terminus (trailer) of the genomic RNA contain the cis-acting sequences important for replication, transcription, and packaging of viral RNA (10). RNA replication occurs when the polymerase somehow switches to a readthrough mode in which the transcription signals are ignored. This produces a complete encapsulated positive-sense replicative intermediate which serves as the template for progeny genomes. A schematic of the genetic map of NDV genomic RNA is shown in FIG. 1.

Vaccination has been widely used to control Newcastle disease. The most commonly used method of vaccination has been the exposure of chickens to low virulence strains of NDV. Advantages of live Newcastle disease vaccines are that they can be mass-applied by natural routes of infection and that protection occurs very soon after application resulting in local as well as systemic immunity.

The main disadvantage of live Newcastle disease vaccines is that they can cause disease and can lead to mortality. Thus, development of a completely apathogenic NDV vaccine would be beneficial to the poultry industry. Before the present invention was made, there was no method available to directly manipulate the genome of NDV to achieve a desired level of attenuation.

A few years ago, two alternative approaches were developed for nonsegmented negative-stranded RNA viruses. In one approach, synthetic "minigenomes" consisting of genomic terminal sequences surrounding a reporter gene were transcribed from cDNA in vitro and transfected into cells infected with wild type helper virus. The second approach involved co-expression of minigenomes and necessary nucleocapsid proteins from transfected plasmids using the transient vaccinia virus/T7 RNA polymerase expression system. These approaches have made it possible to begin the characterization of cis- and trans-acting factors required for transcription and replication of several nonsegmented negative-stranded RNA viruses. Recently, the second approach was used to recover complete infectious recombinant virus from full-length cDNA for several nonsegmented negative-strand RNA viruses, namely, rabies virus, vesicular stomatitis virus, measles virus, Sendai virus, human respiratory syncytial virus, rinderpest virus and parainfluenza 3 virus.

Another major disadvantage of currently available NDV vaccines is that the avirulent vaccine viruses can change to virulent viruses by reversion of up to a few, e.g. one or two, nucleotides at the cleavage site. For instance, currently available NDV vaccines that are of low virulence strains differ from virulent strains by only one or two nucleotides in the $F_0$ protein cleavage site, which is fifteen nucleotides long. Therefore, reversion of these few nucleotides can change the phenotype of the NDV from low virulence to highly virulence. Recently, it was shown that an outbreak of Newcastle disease in Australia was caused by a mutation in the cleavage site on $F_0$ protein of pre-existing avirulent field strains circulatory in eastern Australia (XI International Congress of Virology Abstracts, VET.06, pp. 102).

SUMMARY OF THE INVENTION

A part of the present invention is based on the new idea that, since the genomes typically contain many changes, the ability to directly engineer mutations into cDNA would make it possible to generate defined attenuated strains where cDNA would serve as a stable vaccine "seed."

As discussed above, one of limitations of currently used live attenuated vaccines is their reversion to virulence. One of the aims of the present invention is to overcome this limitation of reversion to virulence by designing attenuating mutation(s) in the genome, which is less likely to revert back to virulence.

Sequence analysis of several avirulent strains shows that attenuation in NDV occurs by three different mechanisms: (1) avirulent strains have few basic amino acid residues, x-Arg/Lys-x-x-Arg, at the $F_0$ protein cleavage site, whereas virulent strains have multibasic residues, Arg-Arg-x-Arg/Lys-Arg, at the $F_0$ protein cleavage site, (2) in some avirulent strains the open reading frame of the HN glycoprotein extends beyond the C terminus of more virulent strains and this terminal extension was assumed to be responsible for the origin of the HN precursor ($HN_0$) found in avirulent strains, and (3) in some avirulent strains a leucine residue is present at the N terminus of the $F_1$ cleavage fragment in place of a phenylalanine residue at this position in virulent strains. Of the three mechanisms, the number of basic residue at the $F_0$ protein cleavage site is the major determinant of NDV virulence. It is thought that those strains with few basic residues at the cleavage site are cleaved only by the proteases of the Clara cells in the bronchial epithelium whereas those strains with multibasic residues at the cleavage site are cleaved by the protease furin present in cells throughout the animal.

In one embodiment of the present invention, the genetic codes of the amino acids in the cleavage site of NDV are changed to make recombinant NDV strains containing the same amino acids as other avirulent strains but will require reversion of several, e.g. 3, 4, 5 or 6, nucleotides before the avirulent recombinant NDV strains are reverted to virulent strains. In another embodiment of the present invention, NDV vaccines are produced that contain the presence of leucine in the +1 position as a mechanism of attenuation. In still another embodiment of the present invention, NDV vaccines are produced that contain cleavable HN protein as a mechanism of attenuation. Within the scope of the present invention are NDV vaccines that work with two or three of these three attenuation mechanisms: (1) having the same amino acid sequence as other avirulent strains that require reversion of several, e.g. 3, 4, 5 or 6, nucleotides before reversion from avirulence to virulence occurs, (2) having leucine in the +1 position, and (3) having a cleavable HN protein. With the present invention's methods of direct manipulations of the NDV genome, production of these NDV vaccines of avirulent strains is possible for the first time.

With the methods of the present invention, the following products are developed:
(i) genetically engineered NDV vaccines that are more stable than currently available NDV vaccines;
(ii) genetically engineered NDV vaccines that are completely apathogenic;
(iii) multivalent genetically engineered NDV vaccines carrying immunogens for influenza virus, infectious bursal disease virus, rotavirus, infectious bronchitis virus, infectious laryngotrachetis virus, chicken anemia virus, Marek's disease virus, avian Leukosis virus and avian adenovirus; and
(iv) genetically engineered NDV stains that carry avian cytokine genes.

The present invention includes a method to produce infectious NDV from cloned cDNA. This method can be used to directly manipulate the genome of NDV. The method can also be used to engineer attenuated NDV vaccine strains by combining two or all of the three mechanisms of attenuation. Furthermore, the present inventor has designed nucleotide sequences at the cleavage site, which are less likely to revert back to virulence.

The present inventor recovered infectious NDV from cloned cDNA using a reverse genetics approach. This approach involves co-expression of full-length NDV genome and nucleocapsid proteins (NP, P and L) from transfected plasmids using the vaccinia virus/T7 RNA polymerase expression system. Within the scope of the present invention is a method to recover NDV with amino acid changes at the cleavage site. The codon of the changed amino acid is different from that of the original amino acid by at least two nucleotides. Such a difference in at least two nucleotides stabilizes the viral genome against reversion from a nonbasic amino acid residue to a basic amino acid residue. For instance, NDV with some or all of following changes at the cleavage site can be produced:

1. NDV in which the arginine residue (AGA) at the −2 position in the cleavage site has been changed to a serine residue (TCC).
2. NDV in which the arginine residue (AGG) at the −5 position in the cleavage site has been changed to a serine residue (TCC).
3. NDV in which the arginine residues at the −2 and −5 positions have been changed to serine residues (TCC).
4. NDV which contains serine (TCC) at the −2 and −5 position and leucine (CTC) at the +1 position.

The above changes are done not only in full-length cDNA clones of NDV Strain Beaudette C, but also in full-length cDNA clones of NDV Strain Ulster which has a cleavable HN protein. The genetically engineered NDV strains of the present invention are completely apathogenic and will not revert back to virulence phenotypes. These new NDV vaccine strains are better than the currently available NDV vaccines.

In addition to the development of live attenuated vaccines against Newcastle disease, this invention can lead to the development of vaccines against other poultry diseases. For example, genetically engineered NDV carrying VP2 protein of infectious bursal disease virus can be used as a bivalent vaccine in chickens.

BRIEF DESCRIPTION OF DRAWINGS

FIG. 3 shows the nucleotide sequences of the leader (SEQ ID NO: 12) and trailer (SEQ ID NO: 13) regions of NDV strain B1 in comparisons with corresponding sequences from NDV strain Beaudette C (SEQ ID NOS 11 and 9 are the leader and trailer respectively) and NDV strain D26 (SEQ ID NO: 10).

FIG. 4 shows the structure of a NDV RNA analog.

FIG. 5A demonstrates NDV minigenome transcription by CAT activity.

FIG. 5B demonstrates NDV minigenome replication by Northern hybridization.

FIG. 7 shows the transcription of NDV-CAT(−) minigenome in response to NDV N, P, and L proteins.

FIG. 9. Schematic procedure for the rescue of infectious NDV from full-length cDNA.

FIG. 10. Photomicrographs of immunological plaques of a laboratory NDV strain Beaudette C (A) and recombinant NDV strain Beaudette C (B).

FIG. 12. Recombinant NDVs showing location of cleavage site mutations (SEQ ID NOS 14 and 15).

FIG. 13. Construction of a recombinant NDV cDNA that contains an extra gene, chloramphenical acetyltransferase (CAT).

FIG. 16. Single-step growth curve of parental and recombinant NDV.

FIG. 17. Multi-step growth curve of parental and recombinant NDV.

DETAILED DESCRIPTION OF THE INVENTION

The present invention have at least the following accomplishments: (1) the complete sequence of the genomic RNA of NDV strain Beaudette C was determined; (2) the leader and trailer sequences of the low virulence NDV strain B1 were determined; (3) cDNAs for all six NDV genes were placed into T7-based expression vectors; (4) subgenomic cDNAs spanning the entire NDV genome were cloned and sequenced; (5) minigenome systems for NDV were developed; (6) information from minigenome systems was developed for rescuing infectious NDV from full-length cDNA; and (7) panels of monoclonal antibodies to NDV proteins were produced.

A. Completion of the Entire Genome Sequence of NDV

Nucleotide sequences of several genes for different NDV strains were available in the prior art, but the complete genomic sequence was not established. In this respect, the Beaudette C strain of NDV has been the most well-characterized, with some of the nucleotide sequences already available:

(1) the complete nucleotide sequence of five genes, namely, P (Daskalakis et al, *Nucleic Acids Res.*, vol. 20, p. 616, 1992), M (Chambers et al, *Nucleic Acids Res.*, vol. 14, pp. 9051-9061, 1986), F (Chambers et al, *J. Gen. Virology*, vol. 67, pp. 2685-2694, 1986), HN (Millar et al, *J. Gen. Virology*, vol. 67, pp. 1917-1927, 1986), and L (Yusoff et al, *Nucleic Acids Res.*, vol. 15, pp. 3961-3976, 1987);

(2) a partial sequence, i.e. the first 192 nucleotides, of the NP gene (Kurilla et al, *Virology*, vol. 145, pp. 203-212, 1985);

(3) the sequences of the intergenic regions in the F-HN junction (Chambers et al, *J. Gen. Virology*, vol. 67, pp. 2685-2694, 1986) and HN-L junction (Chambers et al, *J. Gen. Virology*, vol. 67, pp. 475-486, 1986);

(4) the sequence of the leader region (Kurilla et al, *Virology*, vol. 145, pp. 203-212, 1985); and (5) a partial sequence, i.e. the first 49 nucleotides, of the trailer sequence (Yusoff et al, *Nucleic Acids Res.*, vol. 15, pp. 3961-3976, 1987).

Figure 1:
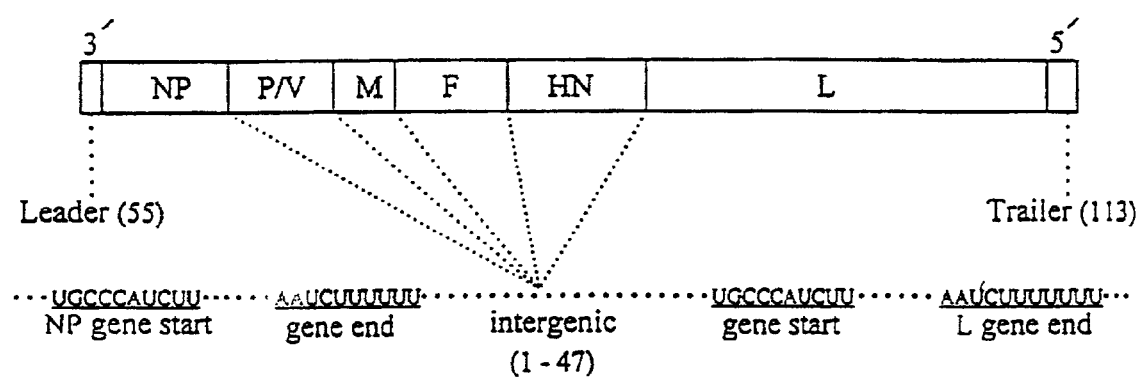
FIG. 1 is a schematic of the genetic map of NDV genomic RNA (SEQ ID NOS 1 and 2).
Figure 2:
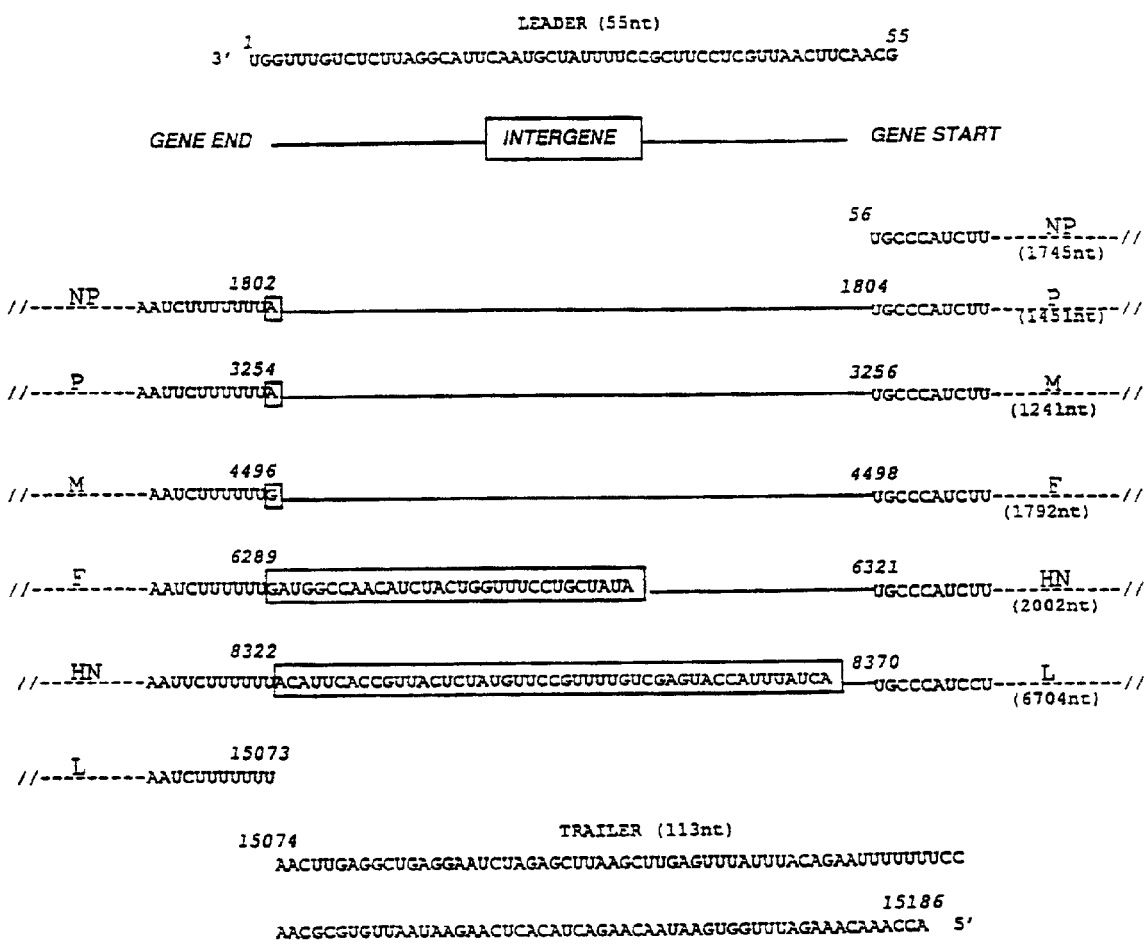
FIG. 2 is the complete map of the genome of NDV strain Beaudette C, wherein the nucleotide sequence of the NP region is available from the GenBank database with the accession number AF064091 (SEQ ID NO: 3 is shown at the top, SEQ ID NOS 4-8, and 2 are shown on the left side, respectively in order of appearance, SEQ ID NO: 1 is shown on the right side, and SEQ ID NO: 9 is shown on the bottom of the figure).

Previous to the present invention, the 5' trailer sequence of NDV was never determined. For the first time, the present inventor determined the 5' trailer sequence of NDV, as well as the nucleotide sequences for the NP gene and the NP-P, P-M and M-F intergenic regions, of the Beaudette C strain to complete the entire nucleotide sequence of the Beaudette C strain of NDV (FIG. 2, in genome RNA-sense). In FIG. 2, the last nucleotide of the gene end, the first nucleotide of the gene start and the first and last nucleotides of the leader and trailer are numbered. The sequences of the leader were derived from Kurilla et al (*Virology*, vol. 145, pp. 203-212, 1985); the intergenic region in the F-HN junction from Chambers et al (*J. Gen. Virology*, vol. 67, pp. 2685-2694, 1986) and the intergenic region in the HN-L junction from Chambers et al (*J. Gen. Virology*, vol. 67, pp. 475-486, 1986). The gene end and gene start sequences of NDV were derived from the published sources of the respective genes. The present invention includes the nucleotide sequences of the complete NP gene, the entire trailer region and the intergenic regions in the NP-P, P-M and M-F junctions.

NDV strain Beaudette C was received from the National Veterinary Services Laboratory at Ames, Iowa, U.S.A. and was propagated in the allantoic cavity of embryonated chicken eggs. The virus was purified as described previously (Kingsbury, *J. Mol. Biol.*, vol. 18, pp. 195-203, 1966). The virion RNA was extracted using proteinase K and TRIzol reagent (Life Technologies). The NP gene, intergenic regions and 5' trailer region were obtained by RT-PCR of the virion RNA. The cDNAs were synthesized using Superscript II reverse transcriptase (Life Technologies). The cDNA corresponding to the NP gene was synthesized using a positive-sense primer, 5' GAAGGTGTGAATCTCGAGT-GCG (SEQ ID NO: 16), complementary to the established sequence at the start of the NP gene. This primer and a negative-sense primer corresponding to the 3' end of the P gene, 5' GCTCGTCGATCTCCGCATCTGT (SEQ ID NO: 17), were used in PCR with high fidelity Pfu DNA polymerase (Stratagene). The PCR product was cloned and sequenced by the dideoxynucleotide chain termination method. For obtaining cDNAs corresponding to the intergenic regions, the positive-sense oligonucleotide primer was derived from a sequence upstream of the respective gene junction. Likewise, the negative-sense primer was derived from a sequence downstream of that gene junction. The PCR product was cloned and sequenced by the dideoxynucleotide chain termination method.

The 5' trailer region was cloned using the 5' RACE method (Dorit, in *Current Protocols in Molecular Biology*, vol. 2, pp. 15.6.1-15.6.10, 1995). Briefly, a positive-sense primer, 5' CACTAAGGACATACTTGAAGC (SEQ ID NO: 18), complemenatry to the downstream end of the L gene was extended with reverse transcriptase and the resulting cDNAs were tailed with dCTP, and separately with dGTP, using terminal deoxynucleotidy transferase. The cDNAs were then amplified by PCR by using the L gene-specific primer described above and either oligo(dG) primer for reactions tailed with dC, or oligo(dC) primer for reactions tailed with dG. The PCR products were then cloned and sequenced by the dideoxynucleotide chain termination method. Tailing reactions with C and G residues assured unambiguous determination of the 5' terminal nucleotide. To sequence the 3' leader region, virion RNA was ligated to a synthetic RNA, and cDNA was made using RT-PCR. The PCR product was cloned and sequenced by the dideoxynucleotide chain termination method.

The complete nucleotide sequence of the NP gene of the NDV strain Beaudette C is 1747 nucleotides long, including non-coding regions of 66 nt at the 3' end and 211 nt at the 5' end of the gene (the nucleotide sequence of the NP region is available from the GenBank database with the accession number AF064091). The major open reading frame of 1467 nt, extending from positive 122 to 1588 of the genomic RNA sequence, contained a coding region of 489 amino acid residues. The NP protein of Beaudette C strain showed 96% amino acid sequence identity with the NP proteins of two lentogenic NDV strains D26 and U2C. The 5' non-coding region of the NP gene of Beaudette C strain showed 31% and 29% sequence variation with the corresponding regions of strains D26 and U2C, respectively. Each of the intergenic regions in the NP-P, P-M and M-F junctions has only one nucleotide. The trailer sequence is 113 nt long in strain Beaudette C (FIG. 2).

Within the scope of the present invention are the nucleotide sequences of the leader and trailer regions of lentogenic NDV strain B1 (FIG. 3). FIG. 4a compares the nucleotide sequences of the leader regions of NDV strain B1 and NDV strain Beaudette C, and the previously published sequence of the leader region of NDV strain D26, in which identical nucleotides are indicated by asterisks. Nucleotides in the leader sequence of strain D26 that are different from those of strain B1 are underlined. FIG. 3b compares the trailer sequences from NDV strain B1 and strain Beaudette C, in which identical nucleotides are indicated by asterisks. The trailer region of strain B1 is 114 nt long, 1 nt longer than the trailer sequence of strain Beaudette C (FIG. 3b). The two sequences show a high level of identity, with only 7 nt differences throughout. The 5' terminal 22 nt are identical in the two sequences.

B. Cloning of NDV Genes into T7-Based Plasmid Vectors cDNAs of all six genes of NDV strain Beaudette C were placed into T7-based plasmid vectors. NDV genes were synthesized by RT-PCR and forced cloned into plasmid pTM-1. RT reactions were carried out using gene specific primers and superscript II RT (Life Technologies). High fidelity Pfu DNA polymerase (Stratagene) was used in PCR. The L gene was first synthesized in two different RT-PCR fragments. Then the two fragments were joined using a unique Afl II restriction site at positions 3026 in the L gene sequence. All genes were partially sequenced and correct expression was confirmed using rabbit reticulocyte lysate system (Promega).

Also, the N, P and L genes were found to be functional using a plasmid based NDV minigenome system.

C. Identification of Cis-Acting Sequences Required for Transcription and Replication of NDV RNA.

Figure 4:
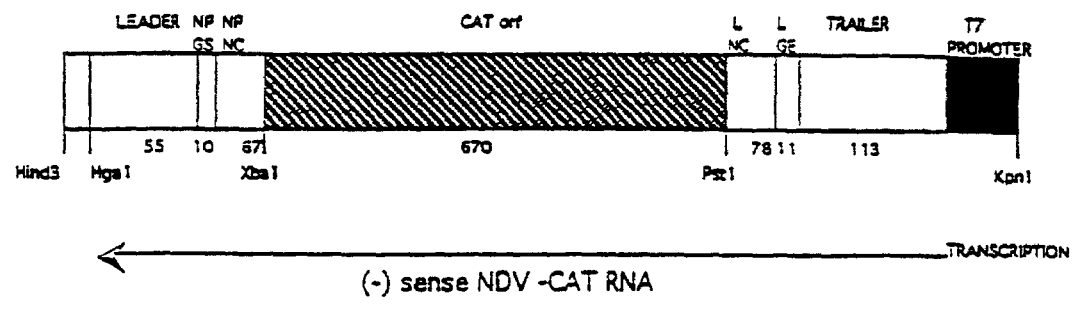

Another aspect of the present invention is the identification of the cis-acting signals required for NDV RNA transcription, replication, and packaging using an RNA based system. Briefly, a cDNA was constructed to encode a 978-nucleotide, internally deleted version of NDV genomic RNA, NDV(–), in which the viral genes were replaced with the bacterial chloramphenicol acetyl transferase (CAT) reporter gene (FIG. 4). The CAT gene was flanked in turn by sequences representing (i) noncoding sequences of the first and last genes in the NDV genome, (ii) NDV gene-start and, gene-end sequences, (iii) 3' leader and 5' trailer sequences of NDV genomic RNA.

C. Rescue of NDV Minigenome

NDV(–) RNAs were synthesized in vitro by run off transcription with T7 RNA polymerase and transfected into NDV-infected chick embryo fibrolast DF1 cells (a gift of D. N. Foster, University of Minnesota). NDV(–) RNA was amplified, expressed, and packaged into RNAse resistant particles that could be used to infect fresh cells (FIGS. 5a and 5b).

A heterologous paramyxovirus, bovine parainfluenze virus 3, failed to rescue NDV-CAT RNA. Passage of NDV minigenome particles were specifically neutralized by NDV antiserum. This procedures provides a sensitive system for characterizing the cis-acting nucleotide sequences required for transcription, replication, and packaging of NDV genomic RNA. The results in FIG. 5 showed that the 3' to 5' ends of NDV genomic RNA contain all the cis-acting sequences required for transcription and replication of NDV RNA. In other words, the leader and trailer sequences were functional.

The present inventor also discovered, using this system, that (i) MDBK, HEp 2, HeLa, 293, and vero cells also rescued NDV minigenome, (ii) higher multiplicity of infection (>10 PFU) of superinfecting NDV had deleterious effect on rescue of NDV minigenome, (iii) time of superinfection with NDV (0-2 hours before transfection) had no effect on rescue of NDV minigenome, and (iv) removal of 3' terminal U residue had no deleterious effect on minigenome rescue.

D. Evaluation of the Rule of Six in NDV

RNA replication by certain paramyxoviruses is efficient only if the nucleotide length of the genome is a multiple of six (the "rule of six"). This rule holds for Sendai virus, measles virus, and parainfluenza virus but does not hold for rabies virus, vesicular stomatitis virus, and respiratory syncytial virus. Interestingly, the genome of NDV strain Beaudette C is 15,186 nucleotides which is a multiple of six. To determine whether NDV follows the rule of six, three additional NDV minigenomes of 976, 980, and 981 nucleotides were constructed by changing the number of nucleotides in the NP noncoding region of the original NDV minigenome. These minigenomes represented multiples of 2 through 10. It was observed that the genome length of NDV must be a multiple of six for efficient transcription, replication, and packaging. This information is useful in the construction of full length NDV and cDNA.

Figure 6:
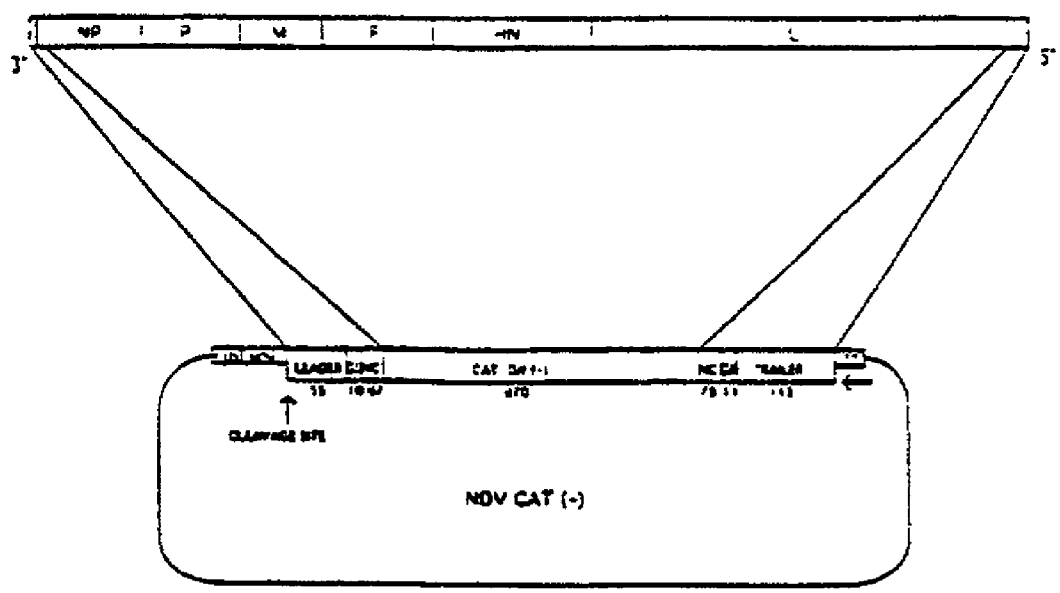
FIG. 6 shows a cDNA-encoded NDV-CAT(−) minigenome.

E. Identification of Trans-Acting Proteins Required for Transcription and Replication of NDV RNA NDV-CAT(–) cDNA was constructed to encode a 978 nucleotide negative-sense NDV-CAT RNA or minigenome, containing the CAT gene flanked by gene-start and gene-end sequences and by the genome termini. A schematic of NDV-CAT(–) is shown in FIG. 6. A NDV(–) minigenome was modified to contain an 84-nucleotide hepatitis delta virus antigenome ribozyme sequence at the leader end to execute self-cleavage to generate nearly exact 3' end. A plasmid containing the HDV ribozyme sequence followed by T7 transcription terminator was used to construct NDV-CAT(–) by PCR.

Figure 7:
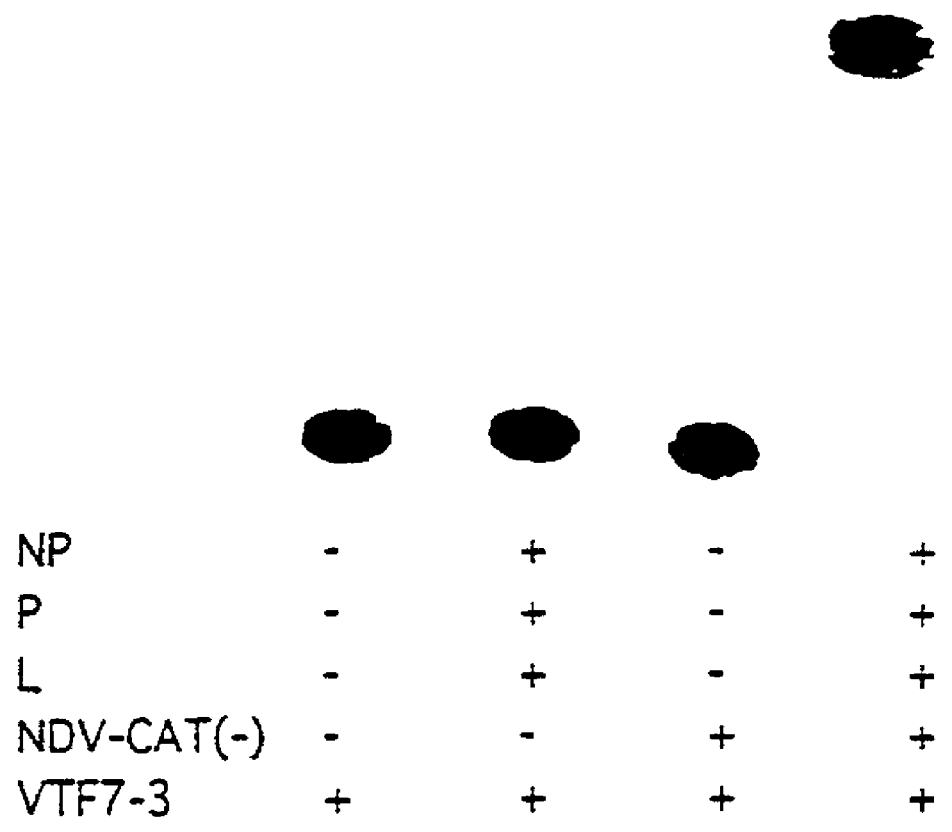

NDV-CAT(–) cDNA was transfected into DF1 cells infected with a vaccinia virus recombinant expressing T7. RNA polymerase, together with plasmids encoding NDV NP, P, and L proteins each under the control of a T7 promoter. Assay of cell lysate 48 hours after transfection showed expression of CAT (FIG. 7), indicating transcription and replication of NDV minigenome. Omission of any of the three viral proteins abrogated transcription and replication, thereby defining the N, P, L proteins are the minimal trans-acting proteins required for transcription and replication of NDV RNA. These results show that infectious NDV can be produced from cloned cDNA.

F. Construction of a Full-Length NDV cDNA Clone.

Figure 8:
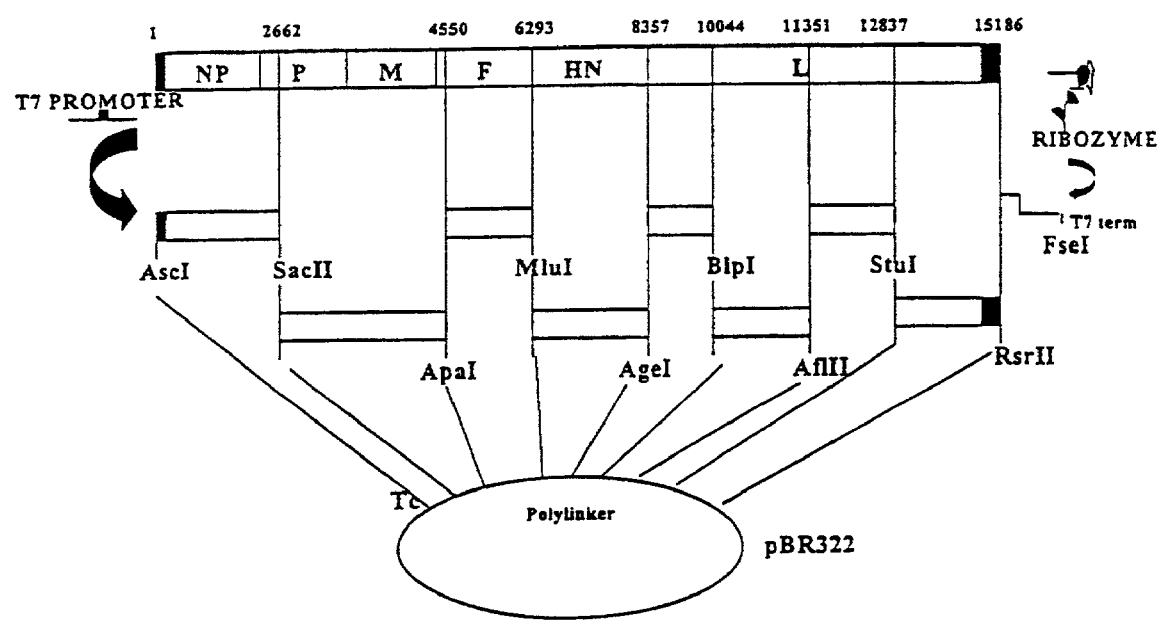
FIG. 8. Construction of NDV Strain Beaudette C antigenomic cDNA.

A cDNA clone encoding the entire 15,186-nt antigenome of NDV strain Beaudette C was constructed from eight cDNA segments that were synthesized by RT-PCR from virion derived genomic RNA (FIG. 8). Each cDNA segment was completely sequenced before assembly into the full-length cDNA clone. The leader end was constructed to join the promoter for T7 RNA polymerase. To generate a nearly exact 3' end, the trailer end was constructed to join hepatitis delta virus antigenome ribozyme sequence followed by tandem terminators of T7 transcription. Two restriction site markers were introduced into the antigenomic cDNA by incorporating the changes into the oligonucleotide primers used in RT-PCR. This was done to identify recombinant virus. An Mlu I site was created in the F-HN intergenic region and the other unique Age I site was created in the HN-L intergenic region.

Within the scope of the present invention is a method of producing NDV produced from cDNA, e.g. full length cDNA (see FIG. 9 for a schematic representation of one of the embodiments of the method). The method comprises the following steps:

(1). providing a plasmid comprising a promoter and a cDNA encoding the antigenome of NDV;

(2). providing a plasmid comprising the gene for NDV NP protein under the control of a promoter;

(3). providing a plasmid comprising the gene for NDV P protein under the control of a promoter;

(4). providing a plasmid comprising the gene for NDV L protein under the control of a promoter;

(5). transfecting cells in a medium with a mixture of the plasmids of steps (1)-(4); and thereafter (6). isolating NDV from the cells or the medium.

In a preferred embodiment of the method, a leader end of the cDNA in step (1) is joined with a promoter for T7 RNA polymerase, the promoter in steps (2)-(4) are promoters for T7 RNA polymerase, and the cells in step 5 are also transfected with vaccinia virus that expresses T7 RNA polymerase. In a more preferred embodiment of the method, a leader end of the cDNA in step (1) is joined with a promoter for T7 RNA polymerase and a trailer end of the cDNA in step (1) is joined with hepatitis delta virus antigenome ribozyme sequence followed by tandem terminators of T7 transcription, the promoter in steps (2)-(4) are promoters for T7 RNA polymerase, and the cells in step 5 are also transfected with vaccinia virus, e.g. strain MVA, that expresses T7 RNA polymerase. In the method of production of NDV from cDNA, the cDNA in step (1) can encode for the complete sequence of the antigenome of NDV or a sequence of the antigenome of NDV with some of the nucleotides or genes missing. In another preferred embodiment of the method, the cDNA can contain at least one, e.g. 2 or 3, restriction sites as markers. The cells in step (5) can be animal cells, such as mammalian cells or avian cells, or plant cells, but avian cells, e.g. HEp-2 cells, are preferred because these cells are permissive to NDV but resistant to cytopathic effects of vaccinia virus strain MVA. Cell lines expressing T7 RNA polymerase can be used.

F. Recovery and Characterization of Infectious NDV from cDNA (i) Recovery of Infectious NDV From cDNA Confluent monolayers of HEp-2 cells in six-well dishes were infected with I PFU per cell of recombinant vaccinia virus strain MVA that expresses T7 RNA polymerase (MVA-TI) (a gift of Dr. B. Moss, NIH). A mixture of three plasmids containing the NDV NP, P and L each under the control of the T7 promoter and a fourth plasmid encoding the full-length NDV antigenome was transfected with LipofectACE (Life Technologies). Twelve hours later the medium was replaced with medium containing 40 μg of cytosine arabinoside per ml to inhibit the replication of vaccinia virus. After 4 days the medium supernatant was centrifuged for 10 min. at 14,000×g to remove vaccinia virus and passaged onto fresh HEp-2 cells in presence of cytosine arabinoside is to further inhibit growth of any residual vaccinia virus. The final supernatant after a second passage in HEp-2 cells was plaque assayed on chick embryo fibroblast cell line DF I under 1% agarose. Several NDV plaques were picked and amplified in DF I cells.

(ii) Characterization of Recovered NDV

Figure 11:
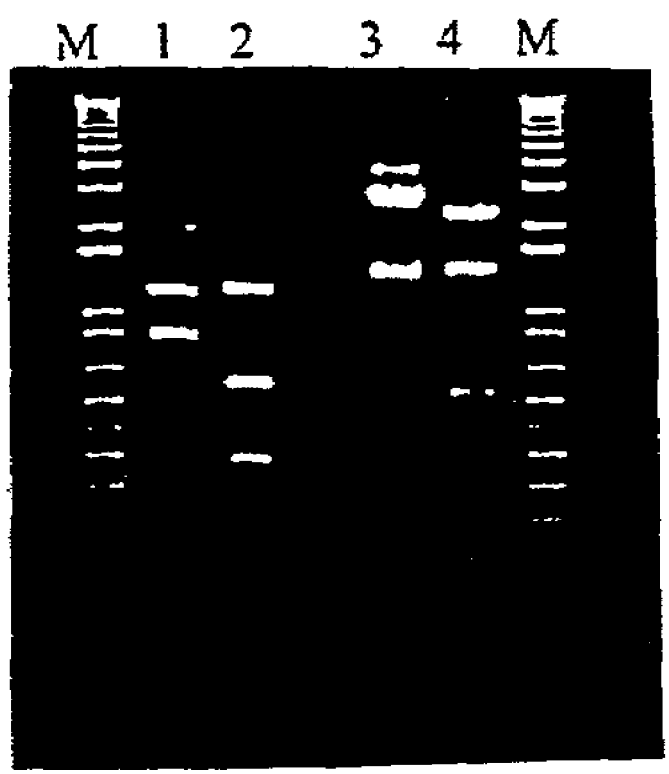
FIG. 11. Identification of sequence markers in recombinant NDV strain Beaudette C by RT-PCR and restriction enzyme digestion.
Figure 16:
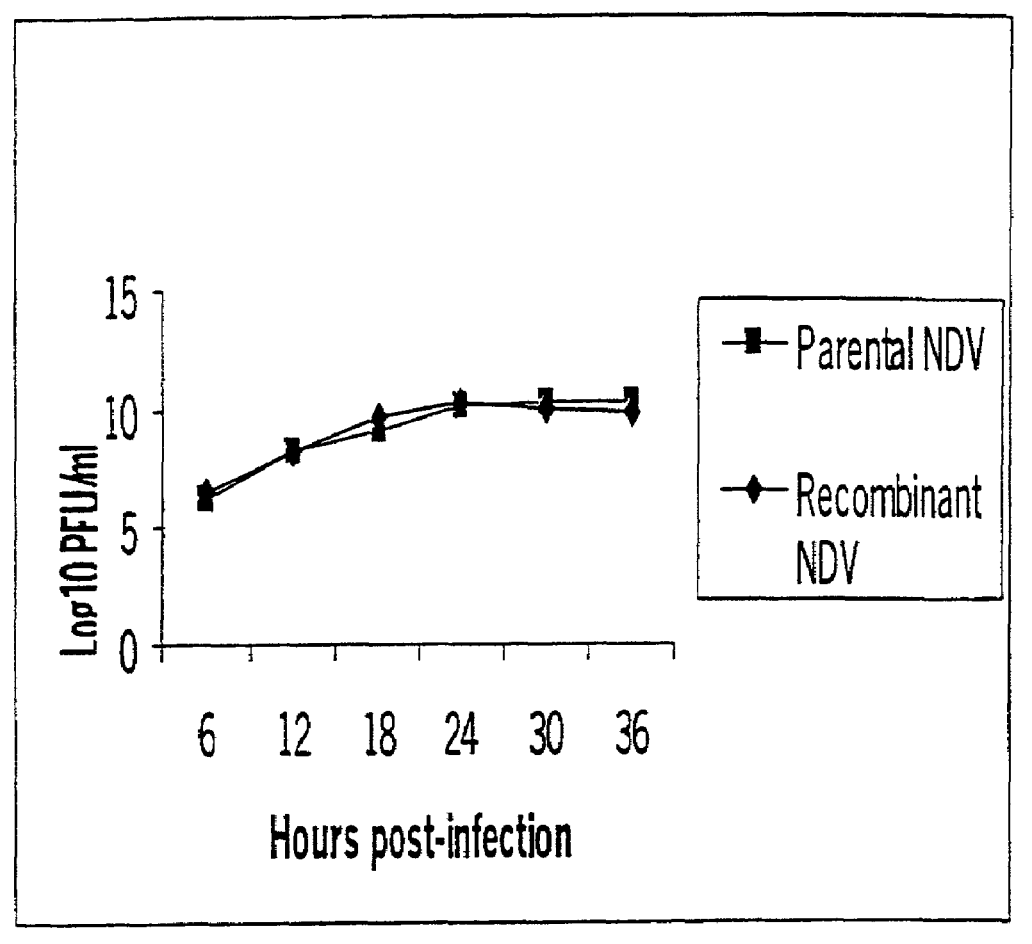
Figure 17:
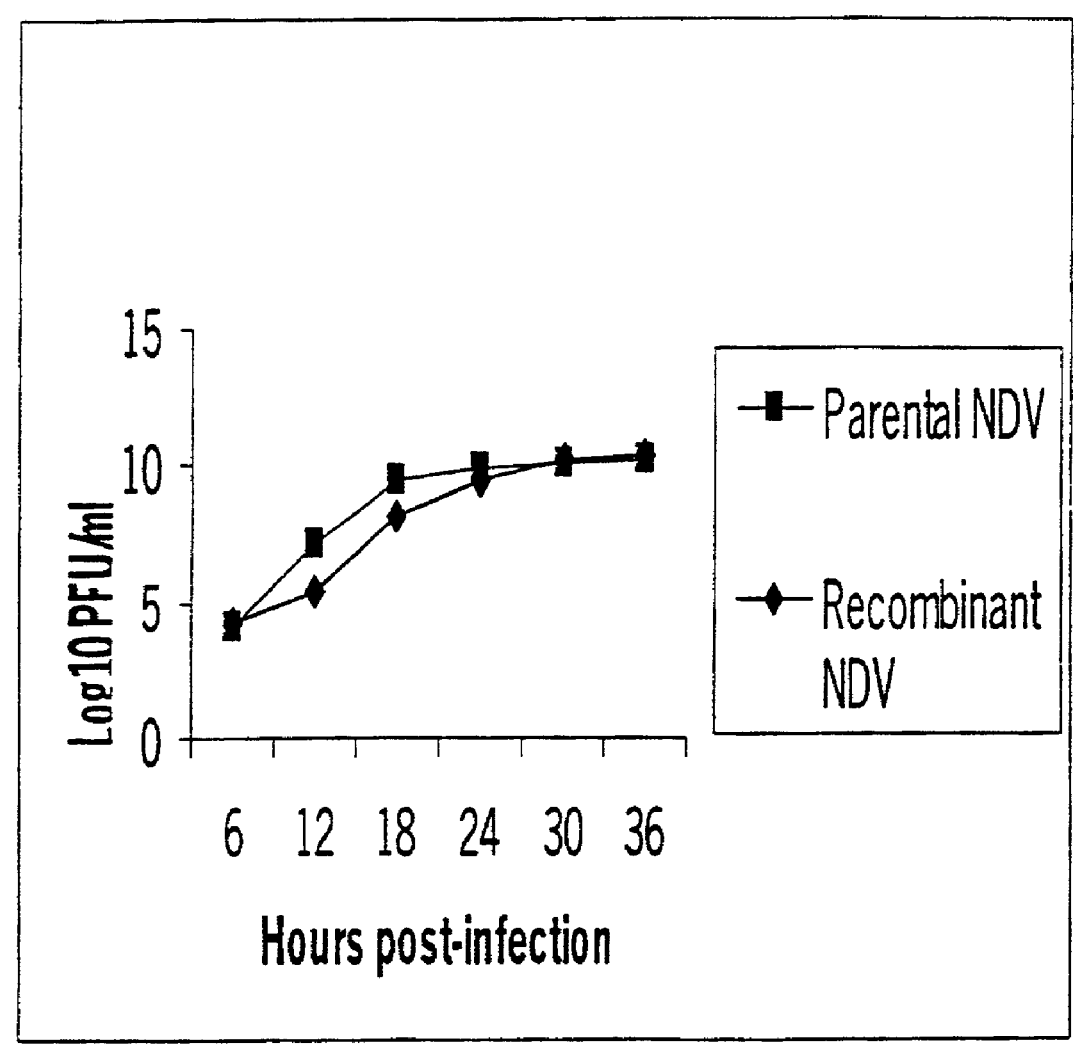

The recovered virus was identified as NDV by plaque assay and positive immunostaining using HN-specific monoclonal antibodies. A comparison of size and morphology of plaques between recovered NDV and laboratory Beaudette C strain did not show any difference (FIG. 10). To verify that the two restriction site markers inserted into the full-length cDNA were present in the recovered NDV, the F-HN and HN-L intergenic regions were amplified by RT-PCR. Restriction enzyme digestion (FIG. 11) showed that the PCR products representing the recombinant virus contained the expected restriction site markers while those representing the laboratory strain did not. In FIG. 11, lane 1 represents Mlu I digested RT/PCR product of laboratory Beaudette C strain across F-HN intergenic region; lane 2 represents Mlu I digested RT/PCR product of recombinant Beaudette C strain across F-HN intergenic region; lane 3 represents Age I digested RT/PCR product of laboratory Beaudette C strain across HN-L intergenic region; and lane 4 represents Age I digested RT/PCR product of recombinant Beaudette C strain across HN-L intergenic region. Control experiments confirmed that the PCR product was dependent on reverse transcription. Nucleotide sequence analysis of cloned PCR products confirmed the sequences spanning the restriction site markers. The growth characteristics of recombinant NDV and wild-type NDV strain Beaudette C were compared in DF I cells. There was no appreciable difference in the growth kinetics between the two viruses (FIGS. 16 and 17). The recombinant NDV strain and the wild-type NDV strain Beaudette C were also studied with NDV antiserum or monoclonal antibodies and the results are shown in Table 1 below.

TABLE 1

| | HI Titers of Antisera and mAbs Titer[a] | | | |
|---|---|---|---|---|
| Strain | NDV Serum | mAb AVS | mAb 15C4 | mAb 10D11 |
| pNDV | 4096 | 8 | 4096 | 256 |
| rNDV | 8192 | 32 | 8192 | 512 |

[a]Expressed as reciprocal of the highest dilution that caused inhibition of haemagglutination. Results for control serum were negative.

The results in Table 1 show that the recombinant NDV, rNDV, and the wild type NDV, pNDV, were immunologically similar.

There was also no difference in the mean death time (MDT) for chicken embryos between the two viruses as shown in Table 2 below.

TABLE 2

| Strain | Mean Death Time in Eggs | Pathotype |
|---|---|---|
| pNDV | 60 hours | Mesogenic |
| rNDV | 62 hours | Mesogenic |
| La Sota | 106 hours | Lentogenic |

G. Construction of NDV with Mutations in the Fusion Protein Cleavage Site

The fusion protein is thought to be the major determinant of the virulence of NDV strains. Cleavability of the precursor fusion protein Fo to F, and F2 in a range of cell types correlates well with the pathogenicity of viral strains in chickens. The differences in cleavability of the Fo protein are thought to be due to sequence differences at the cleavage site. Avirulent strains have few basic amino acid residues (x-Arg/Lys-x-x-Arg) at the $F_0$ protein cleavage site, whereas virulent strains have multibasic residues (Arg-Arg-x-Arg/Lys-Arg) at the Fo protein cleavage site. Furthermore, in some avirulent strains a leucine residue is present at the N terminus of the $F_1$ cleavage fragment in place of a phenylalanine residue at this position in virulent strains. The present inventor examined the role of the sequences at the F protein cleavage site in NDV pathogenesis.

Cleavage site mutants were generated by sequential PCR mutagenesis. cDNA fragments containing the mutations were then assembled into the full-length cDNA clone. Two unique restriction enzyme sites, Apa I (position 4550 in the complete 15,186-nt antigenome sequence) and Not I (position 4953), were used to replace the wild-type fragment containing mutations at the cleavage site. A total of seven NDV mutants representing all possible structures of the cleavage site between velogenic and lentogenic strains were recovered (FIG. 12). Mutant I whose cleavage site is same as lentogenic strains was avirulent to chick embryos by MDT. Where as mutants 2 and 3 were of intermediate virulence to chick embryos by MDT.

H. Recovery of NDV Expressing an Additional, Foreign Gene

Figure 13:
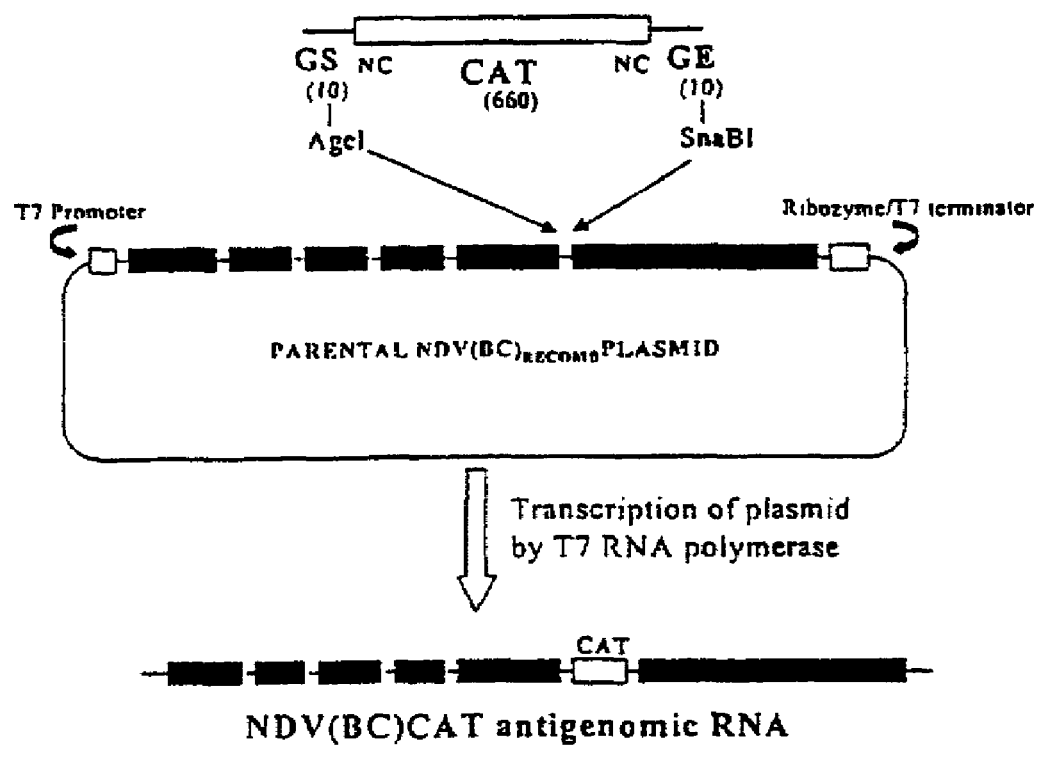
Figure 14:
FIG. 14. Detection of CAT expression after one passage.

The genome of NDV can be used to express an additional gene. For instance, the following experiment showed that the chloramphenicol acetyltransferase (CAT) gene is an example of the additional foreign gene. CAT gene was inserted into the HN-L intergenic region. The sequence in the HN-L intergenic region was modified to contain a unique Sna B I site downstream of the Age I site. The open reading frame (ORF) encoding the CAT protein was engineered to be flanked by the NDV GS and GE signals. This transcription cassette was inserted into the HN-L intergenic region of NDV antigenomic cDNA (FIG. 13). In this construct, care was taken over the genome length requirement called the "rule of six". NDV has a preference but not an absolute requirement for a genome of 6 n length. A recombinant NDV containing the CAT gene was recovered using the strategy described before. RT-PCR of the genomic RNA isolated from the recovered virus showed the presence of the inserted CAT gene. The recovered virus expressed abundant levels of CAT enzyme (FIG. 14, lane 1 shows data from laboratory Beaudette C strain; lane 2 shows data from recombinant Beaudette C strain containing the CAT gene). Analysis of mRNAs by Northern blot hybridization showed that the CAT gene was expressed as an additional, separate, poly(A) mRNA. CAT expression was stable for at least 8 passages, indicating that the activity of the CAT protein encoded by NDV remained unimpaired by mutation. There was no appreciable difference either in plaque phenotype or in growth kinetics between the recovered virus and wild-type laboratory strain. This study showed that NDV can tolerate an increase of genome length of at least 690 nucleotides.

I. Generation of Recombinant Lentogenic NDV Strain LaSota From cDNA

Figure 15:
FIG. 15. Identification of sequence markers in recombinant NDV strain LaSota by RT-PCR and restriction enzyme digestion.

In order for the recombinant NDV to be used as a vaccine vector, the vector itself should not produce any disease. The recombinant NDV strain Beaudette C produced by the present invention is a mesogenic strain. Within the scope of the present invention is the generation of recombinant lentogenic NDV for vector purposes. The present inventor rescued NDV strain LaSota because the complete nucleotide sequence of this strain is available. The NDV strain LaSota was received from Dr. Henry Stone (East Carolina University). This sample was only one egg passage away from the original "NJ LaSota 1953" isolate in the University of Wisconsin collection. A cDNA clone encoding the entire 15,186-nt antigenome of NDV strain LaSota was constructed from seven different cDNA fragments. Each cDNA fragment was completely sequenced before assembly. Comparison of the nucleotide sequence of the LaSota strain used here with the published sequence of NDV strain LaSota showed differences in 27 nucleotides distributed throughout the entire genome. Another difference found was that the L gene of the LaSota strain used here contained a double frameshift resulting in a 28 amino acid difference located in block V. This double frameshift had been found in NDV strain Beaudette C in the prior art and recently had also been reported in NDV strain LaSota in the prior art. Thus, it indicates that the original LaSota strain has undergone genetic changes probably due to point mutations. To verify the recovery of NDV strain LaSota from cDNA, the nucleotide sequences were altered to create a Mlu I site in the F-HN intergenic region and Sna B I site at HN-L intergenic region. These two sites are not present either in laboratory LaSota strain or in NDV Beaudette C strain. Recovery of recombinant NDV strain LaSota was carried out using the method described before except that the supernatant after transfection was inoculated into the allantoic cavity of 10-day-old embryonated chicken eggs to amplify the recovered recombinant virus. RT-PCR of genomic RNA of recombinant NDV strain LaSota across these sites confirmed that the recovered virus was NDV strain LaSota (FIG. 15, in which lane 1 represents PCR of F-HN intergenic region of recombinant LaSota strain without RT; lane 2 represents RT/PCR of F-HN intergenic region of recombinant LaSota strain; lane 3 represents Mlu I digestion of lane 2 product; lane 4 represents PCR of F-HN intergenic region of laboratory LaSota strain without RT; lane 5 represents RT/PCR of F-H N intergenic region of laboratory LaSota strain; and lane 6 represents Mlu I digestion of lane 5 product).

In one of the embodiments of the present invention, infectious NDV was produced by the intracellular coexpression of four plasmid-borne cDNAs. One cDNA encoded a complete positive-sense version NDV genome, and each of the other three encoded a separate NDV protein, namely the nucleocapsid protein (NP), the phospoprotein (P) and the large protein (L). Each cDNA in the plasmid was under the control of a T7 RNA promoter. The full-length cDNA of NDV Strain Beaudette C was assembled by ligation of eight different RT-PCR fragments. Monolayer cultures of HEp-2 cells were infected with vaccinia virus Strain MVA expressing T7 RNA polymerase and transfected with the four different plasmids. On day 3 clarified medium supernatants were passaged onto fresh chick embryo fibroblast cells and overlaid with agarose for plaque purification. Individual NDV plaques were picked passaged in fresh chick embryo fibroblast cells. Our results showed NDV was produced when all four plasmids were used in transfection. NDV was not produced if any of the four plasmid was omitted. Recovery of NDV from cDNA was verified by (i) the presence of two genetic tags generating restriction sites in cDNA derived from the genome and (ii) and direct sequencing of the genomic RNA of the recovered virus. These results show that recombinant NDV can be recovered from cDNA and the genome of NDV can be manipulated at the cDNA level.

In the present invention, the genome of NDV can be directly manipulated. With the manipulation of the genome of NDV, one can (i) introduce multiple attenuation mutations to create stable vaccine virus, (ii) create new types of attenuation mutations, which might include deletion of the viral genome, (iii) change the cleavage site of F and HN proteins to create completely apathogenic vaccine strains, (iv) change the gene order of the virus so the immunogenic proteins are expressed in large amounts, (v) modify vaccine virus to accommodate antigenic drift in circulating virus, (vi) the length of the intergenic sequences can be changed to create attenuating viruses, (vii) create NDV that does not express V protein, and (viii) insert foreign sequences into the NDV genome for coexpression. For example, the gene for protective antigen of another avian pathogen or the genes for avian cytokines can be inserted into the NDV genome for coexpression.

In the present invention, production of infectious NDV from cloned cDNA will be useful to (i) provide stable vaccine seed, (ii) introduce attenuation mutations into the genome of NDV to create stable, completely apathogenic vaccine virus strains, (iii) engineer NDV carrying foreign genes. For example, the gene for protective antigen of another avian pathogen or the genes for cytokines can be inserted into the NDV genome for coexpression.

Also within the scope of the present invention are the products listed below.
  (i) A genetically engineered NDV vaccine that is better than currently available NDV vaccines.
  (ii) Multivalent genetically engineered NDV vaccines carrying immunogens for influenza virus, infectious bursal disease virus, rotavirus, infectious bronchitis virus, infectious laryngotracheitis virus, chicken anemia virus, Marek's disease virus, avian Leukosis virus and avian adenovirus.
  (iii) A genetically engineered NDV carrying avian cytokine genes.

Within the scope of the present invention are an isolated nucleic acid encoding the entire genome of NDV Beaudette C strain ("isolated" herein means a substantially purified nucleic acid or, optionally, a substantially purified nucleic acid without the proteins of NDV Beaudette C strain), the 5' trailer nucleotide sequence of NDV Beaudette C strain, an isolated nucleic acid encoding the NP protein of NDV Beaudette C strain ("isolated" herein means a substantially purified nucleic acid or, optionally, a substantially purified nucleic acid without the proteins of NDV Beaudette C strain), the 5' trailer nucleotide sequence of NDV Beaudette B1 strain, the leading nucleotide sequence of NDV Beaudette B1 strain. Also within the scope of the present invention are vaccines for NDV. These vaccines can be administered orally, intranasally, intraocularly or parenterally, e.g. by intramuscular or subcutaneous injection, to an avian host in need of vaccination against NDV at a dose of $1\times10^4$ $EID_{50}$ to $1\times10^9$ $EID_{50}$ per bird, or preferably $1\times10^5$ $EID_{50}$ to $1\times10^8$ $EID_{50}$ to per bird, or more preferably $1\times10^6$ $EID_{50}$ to $1\times10^7$ $EID_{50}$ per bird (EID means "embryo infective dose"). However, the route of administration and dose can be adjusted, by one skilled in the art, based on the condition of the avian host and the virulence of the NDV that the vaccination is aimed at preventing.

An aspect of the present invention is a synthetic cDNA which encodes an infectious Newcastle Disease Virus (NDV), which is optionally attenuated.

Another aspect of the present invention is a vector containing a synthetic cDNA which encodes an infectious NDV, optionally linked to an operable promoter.

Another aspect of the present invention is a host cell containing a synthetic cDNA which encodes an infectious NDV.

Within the scope of the present invention is a method of producing infectious NDV comprising inserting a synthetic cDNA which encodes an infectious NDV into a host cell, wherein the cDNA is operably-linked to a promoter; and expressing the cDNA in the host cell to produce the infectious NDV.

An embodiment of the present invention is an infectious NDV, produced by the following method: inserting a synthetic cDNA which encodes infectious NDV into a host cell, wherein the cDNA is operably-linked to a promoter; and expressing the cDNA in the host cell to produce the infectious NDV.

Another embodiment of the present invention is a vaccine comprising an infectious NDV which has been attenuated by introducing at least one RNA point mutation thereon, wherein the infectious NDV has been produced by the following method:

inserting a synthetic cDNA which encodes an infectious NDV into a host cell, wherein the cDNA is operably-linked to a promoter; and expressing the cDNA in the host cell to produce the infectious NDV.

Within the scope of the present invention is a vaccine for Newcastle disease comprising a Newcastle disease virus, wherein the Newcastle disease virus has at least two of the features selected from the group consisting of (1) a $F_0$ protein cleavage site having at least two less basic amino acid residues than a $F_0$ protein cleavage site of Newcastle disease virus wild type strain Beaudette C; (2) an amino acid having a non-aromatic side chain at the N terminus of the $F_1$ cleavage fragment, wherein the amino acid having a non-aromatic side chain is glycine, alanine, valine, leucine or isoleucine, preferably leucine; and (3) an open reading frame of a HN glycoprotein being longer than an open reading frame of a HN glycoprotein of Newcastle disease virus wild type strain Beaudette C. Preferably, in the vaccine, the Newcastle disease virus has a $F_0$ protein cleavage site having serine or glycine independently replacing at least two basic amino acid residues of the $F_0$ protein cleavage site of Newcastle disease virus wild type strain Beaudette C. Also preferably, in the vaccine, the $F_0$ protein cleavage site has at least two less basic amino acid residues than a $F_0$ protein cleavage site of Newcastle disease virus wild type strain Beaudette C, wherein said at least two basic amino acid residues are arginine or lysine. In the vaccine, more preferably, the Newcastle disease virus has at least one of the following features: (i) a codon, TCC, for serine in place of the codon for an arginine residue at the −2 position of the $F_0$ protein cleavage site of Newcastle disease virus wild type strain Beaudette C, and (ii) a codon, TCC, for serine in place of the codon for an arginine residue at the −5 position of the $F_0$ protein cleavage site of Newcastle disease virus wild type strain Beaudette C. In the vaccine, more preferably, the Newcastle disease virus has at least one of the following two features: (i) a codon, TCC, for serine in place of the codon for an arginine residue at the −2 position of the $F_0$ protein cleavage site of Newcastle disease virus wild type strain Beaudette C, and (ii) a codon, TCC, for serine in place of the codon for an arginine residue at the −5 position of the $F_0$ protein cleavage site of Newcastle disease virus wild type strain Beaudette C; and has the amino acid, i.e. leucine, having a non-aromatic side chain at the N terminus of the $F_1$ cleavage fragment. More preferably, the codon for the leucine in the cDNA that makes the virus in the vaccine is CTC. Optionally, the Newcastle disease virus in the vaccine carries at least one gene encoding an avian cytokine, e.g. an interleukin such as IL-2 and IL-4.

Also within the scope of the present invention is an isolated nucleic acid comprising a sequence of 15,186 nucleotides as described in FIG. 2.

Another embodiment of the present invention is an isolated nucleic acid of up to 200, 150, 100 or 75 nucleotides in length, comprising a sequence of 55 nucleotides of the leader region described in FIG. 2. Another embodiment of the present invention is an isolated protein encoded by the isolated nucleic acid.

Another embodiment of the present invention is an isolated nucleic acid consisting essentially of or consisting of the sequence of 55 nucleotides of the leader region described in FIG. 2. Another embodiment of the present invention is an isolated protein encoded by the isolated nucleic acid.

Another embodiment of the present invention is an isolated nucleic acid of up to 350, 250 or 150 nucleotides in length, comprising a sequence of 113 nucleotides of the trailer region described in FIG. 2. Another embodiment of the present invention is an isolated protein encoded by the isolated nucleic acid.

Another embodiment of the present invention is an isolated nucleic acid consisting essentially of or consisting of the sequence of 113 nucleotides of the leader region described in FIG. 2. Another embodiment of the present invention is an isolated protein encoded by the isolated nucleic acid.

Another embodiment of the present invention is an isolated nucleic acid of up to 2500 or 2000 nucleotides in length comprising the nucleotide sequence of the NP region described in FIG. 2 (the nucleotide sequence of the NP region is available from the GenBank database with the accession number AF064091). Another embodiment of the present invention is an isolated protein encoded by the isolated nucleic acid.

Another embodiment is an isolated nucleic acid consisting essentially of or consisting of the nucleotide sequence of the NP region is available from the GenBank database with the accession number AF064091. Another embodiment of the present invention is an isolated protein encoded by the isolated nucleic acid.

Within the scope of the present invention is a method of producing infectious Newcastle disease virus, comprising the following steps:

inserting a cDNA encoding the infectious Newcastle disease virus into a host cell, wherein the cDNA is operably-linked to a promoter; and expressing the cDNA in the host cell to product the infectious Newcastle disease virus.

The method preferably further comprises purifying the infectious Newcastle disease virus.

Within the scope of the present invention are vectors containing the cDNA that can be prepared by the methods or information disclosed in this patent application, optionally linked to an operable promoter.

Another aspect of the present invention is a method of preventing or treating Newcastle disease in an avian subject by administering a vaccine against Newcastle disease virus.

The present invention shows that infectious NDV can be recovered from cloned cDNA. Both virulent and avirulent strains of NDV (as demonstrated by Beaudette C and LaSota) can be recovered from cDNAs. The present invention also shows that a foreign gene, chloramphenical acetyltransferase (CAT), can be introduced into the genome of NDV and the CAT protein was expressed in infected cells. Thus, recombinant NDV can be used to express proteins of other avian pathogens. Therefore, the NDV can be used as a vaccine vector. The present invention also presents a method to recover NDV with mutations in the F protein cleavage site. This result shows that the cleavage site of currently used live attenuated vaccines, e.g. LaSota, can mutate to revert back to virulence relatively easily.

REFERENCES

1. Alexander, D. J. (1991). Newcastle Disease and other paramyxoviruses. In: Diseases of poultry, glh ed. Calnek B. W. edited. Iowa State University Press, Ames, Iowa. pp 496-519.
2. Murphy, F. A., Fauquet, C. M., Bishop, D. H. L., Ghabrial, S. A., Jarvis, A. W., Martelli, G. P., Mayo, M. A., and Summers, M. D. (1995). Virus Taxonomy. Sixth Report of the International Committee on Taxonomy of Viruses. Vienna & New York; Springer-Verlag.
3. Krishnamurthy, S. and Samal, S. K. (1997). Nucleotide sequences of the Trailer, Nucleocaspid protein gene and Intergenic regions of Newcastle Disease Virus strain Beaudette C and: Completion of the entire genome sequence. J. Gen. Virol. 79, 2419-2424.
4. Peeples, M. E. (1988). Newcastle disease virus replication. In: Newcastle Disease, Alexander, D. J. edited. Kluwer Academic Published. pp 45-78.
5. Steward, M., Vipond, B., Miller, N. S., and Emmerson P. T. (1993). RNA editing in Newcastle disease virus. J. Gen Virol. 74, 2539-2547.
6. Homma, M. and Ohucei, M. (1973). Trypsin acyion on the growth of Sendai virus in tissue culture cells. IV. Structural difference of Sendai viruses grown in eggs and tissue culture cells. J. Virol. 12, 1457-1465.
7. Meulemans, G., Gonze, M., Carlier, M. C., Petit, A., Bumy, A., and Long, L. (1986). Protective effects of HN and F protein glycoprotein-specific monoclonal antibodies on experimental Newcastle disease. Avian Panthol. 15, 761-768.
8. Morgan, R. W., Gelb, J., Schreurs, L. S., Lutticken, D., Rosenberger, J. K. and Sonderrneijer, P. J. (1992). Protection of chickens from Newcastle and Marek's diseases with a recombinant herpes virus of turkeys vaccine expressing the Newcastle disease virus fusion protein. Avian Dis. 36, 858-870.
9. Steward, M., Samson, A. C. R., Erington, W. and Emerson, P. T. (1995). The Newcastle disease virus V protein binds zinc. Arch Virol. 140, 1321-1328.
10. Lamb, R. A. and Kolakofsky, D. (1996). Pararnyxoviridae: the virusps and their replication. In Fields Virology; 3d ed. Fields, B. N., Knipe, D. M. and Howley, P. M. edited. Philadelphia, Lippincott-Raven.

What is claimed is:

1. A vaccine for Newcastle disease comprising a genetically engineered live attenuated Newcastle disease virus, wherein the genetically engineered live attenuated Newcastle disease virus has a $F_o$ protein cleavage site having at least two less basic amino acid residues than a $F_o$ protein cleavage site of Newcastle disease virus wild type strain Beaudette C, wherein codons of non-basic amino acid residues replacing the at least two basic amino acid residues are different from codons of the basic amino acid residues by at least two nucleotides; and at least one of the features selected from the group consisting of: (1) an amino acid having a non-aromatic side chain at the N terminus of the $F_1$ cleavage fragment, wherein the amino acid having a non-aromatic side chain is glycine, alanine, valine, leucine or isoleucine; and (2) an open reading frame of a HN glycoprotein being longer than an open reading frame of a HN glycoprotein of Newcastle disease virus wild type strain Beaudette C, wherein the genetically engineered live attenuated Newcastle disease virus is in the form of a vaccine for administration to a subject.

2. The vaccine of claim 1, wherein in (1) the genetically engineered live attenuated Newcastle disease virus has the $F_o$ protein cleavage site having serine or glycine independently replacing at least two basic amino acid residues of the $F_o$ protein cleavage site of Newcastle disease virus wild type strain Beaudette C.

3. The vaccine of claim 2, wherein in (1) said at least two basic amino acid residues of the $F_o$ protein cleavage site of Newcastle disease virus wild type strain Beaudette C replaced by serine or glycine are arginine or lysine.

4. The vaccine of claim 3, wherein in (1) the genetically engineered live attenuated Newcastle disease virus has at least one of the following two features: (i) a codon, TCC, for serine in place of the codon for an arginine residue at the −2 position of the $F_o$ protein cleavage site of Newcastle disease virus wild type strain Beaudette C, and (ii) a codon, TCC, for serine in place of the codon for an arginine residue at the −5 position of the $F_o$ protein cleavage site of Newcastle disease virus wild type strain Beaudette C.

5. The vaccine of claim 1, wherein in (2) the amino acid having a nonaromatic side chain is leucine.

6. The vaccine of claim 4, wherein the genetically engineered live attenuated Newcastle disease virus has at least one of the following two features: (i) a codon, TCC, for serine in place of the codon for an arginine residue at the −2 position of the $F_o$ protein cleavage site of Newcastle disease virus wild type strain Beaudette C, and (ii) a codon, TCC, for serine in place of the codon for an arginine residue at the −5 position of the $F_o$ protein cleavage site of Newcastle disease virus wild type strain Beaudette C; and has an amino acid having a non-aromatic side chain at the N terminus of the $F_1$ cleavage fragment, wherein the amino acid having a non-aromatic side chain is leucine.

7. The vaccine of claim 6, wherein the codon for leucine is CTC.

8. The vaccine of claim 1, wherein in (1), the $F_o$ protein cleavage site has at least two less basic amino acid residues than a $F_o$ protein cleavage site of Newcastle disease virus wild type strain Beaudette C, wherein said at least two basic amino acid residues are arginine or lysine.

9. The vaccine of claim 1, wherein the genetically engineered live attenuated Newcastle disease virus carries at least one gene encoding an avian cytokine.

10. The vaccine of claim 9, wherein said cytokine is an interleukin.

* * * * *

SEQUENCE LISTING

<160> NUMBER OF SEQ ID NOS: 18

<210> SEQ ID NO 1
<211> LENGTH: 10
<212> TYPE: RNA
<213> ORGANISM: Newcastle disease virus

<400> SEQUENCE: 1
uucuacccgu                                                              10

<210> SEQ ID NO 2
<211> LENGTH: 10
<212> TYPE: RNA
<213> ORGANISM: Newcastle disease virus

<400> SEQUENCE: 2
uuuuuucuaa                                                              10

<210> SEQ ID NO 3
<211> LENGTH: 55
<212> TYPE: RNA
<213> ORGANISM: Newcastle disease virus

<400> SEQUENCE: 3
gcaacuucaa uugcuccuuc gccuuuuauc guaacuuacg gauucucugu uuggu            55

<210> SEQ ID NO 4
<211> LENGTH: 12
<212> TYPE: RNA
<213> ORGANISM: Newcastle disease virus

<400> SEQUENCE: 4
auuuuuuucu aa                                                           12

<210> SEQ ID NO 5
<211> LENGTH: 12
<212> TYPE: RNA
<213> ORGANISM: Newcastle disease virus

<400> SEQUENCE: 5
auuuuuucuu aa                                                           12

<210> SEQ ID NO 6
<211> LENGTH: 11
<212> TYPE: RNA
<213> ORGANISM: Newcastle disease virus

<400> SEQUENCE: 6
guuuuuucua a                                                            11

<210> SEQ ID NO 7
<211> LENGTH: 41
<212> TYPE: RNA
<213> ORGANISM: Newcastle disease virus

<400> SEQUENCE: 7
auaucguccu uuggucaucu acaaccggua guuuuuucua a                           41

<210> SEQ ID NO 8
<211> LENGTH: 58
<212> TYPE: RNA
<213> ORGANISM: Newcastle disease virus

<400> SEQUENCE: 8
acuauuuacc augagcuguu uugccuugua ucucauugcc acuuacauuu uuucuuaa        58

<210> SEQ ID NO 9
<211> LENGTH: 113
<212> TYPE: RNA
<213> ORGANISM: Newcastle disease virus

<400> SEQUENCE: 9
accaaacaaa gauuggguga auaacaagac uacacucaag aauaauugug cgcaaccuuu       60 uuuaagaca uuuauuugag uucgaauucg agaucuaagg agucggaguu caa              113

<210> SEQ ID NO 10
<211> LENGTH: 66
<212> TYPE: RNA
<213> ORGANISM: Newcastle disease virus

<400> SEQUENCE: 10
uucuacccgu acgacuuucg auugcuccuu cgccuuuuau cguaccuuac agauucucug       60
uuuggu                                                                 66

<210> SEQ ID NO 11
<211> LENGTH: 65
<212> TYPE: RNA
<213> ORGANISM: Newcastle disease virus

<400> SEQUENCE: 11
uucuacccgu gcaacuucaa uugcuccuuc gccuuuuauc guaacuuacg gauucucugu       60
uuggu                                                                  65

<210> SEQ ID NO 12
<211> LENGTH: 65
<212> TYPE: RNA
<213> ORGANISM: Newcastle disease virus

<400> SEQUENCE: 12
uucuacccgu gcgacuucaa uugcuccuuc gccuuuuauc guaacucacg gauucucugu       60
uuggu                                                                  65

<210> SEQ ID NO 13
<211> LENGTH: 114
<212> TYPE: RNA
<213> ORGANISM: Newcastle disease virus

<400> SEQUENCE: 13
accaaacaaa gauuggguga augacgagac uacacucaag aauaauugug cgcaaccuuu       60 uuuaagaca uuuauuugag uucgaauucg aguccuaagg agucagagcu caac             114

<210> SEQ ID NO 14
<211> LENGTH: 33
<212> TYPE: PRT
<213> ORGANISM: Newcastle disease virus

<400> SEQUENCE: 14

Gly Gly Gly Arg Gln Gly Arg Leu Ile Gly Ala Ile Ile Gly Gly Val
 1               5                  10                  15

Ala Leu Gly Val Ala Thr Ala Ala Gln Ile Thr Ala Ala Ala Ala Leu
            20                  25                  30

-continued

Ile

<210> SEQ ID NO 15
<211> LENGTH: 33
<212> TYPE: PRT
<213> ORGANISM: Newcastle disease virus

<400> SEQUENCE: 15

Gly Gly Arg Arg Gln Lys Arg Phe Ile Gly Ala Ile Ile Gly Gly Val
 1               5                  10                  15

Ala Leu Gly Val Ala Thr Ala Ala Gln Ile Thr Ala Ala Ala Ala Leu
            20                  25                  30

Ile

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaggtgtga atctcgagtg cg                                            22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctcgtcgat ctccgcatct gt                                            22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cactaaggac atacttgaag c                                             21